United States Patent [19]

Tenne

[11] 4,221,816
[45] Sep. 9, 1980

[54] METHOD FOR THE CONTROL OF PHYTOPATHOGENIC FUNGI USING P-(ALKOXYALKYL)UREA COMPOUNDS

[75] Inventor: Frank D. Tenne, Plainsboro, N.J.

[73] Assignee: American Cyanamid Company, Stamford, Conn.

[21] Appl. No.: 30,678

[22] Filed: Apr. 16, 1979

[51] Int. Cl.$^2$ ............................................... A01N 9/12
[52] U.S. Cl. .................................. 424/322; 260/553 A
[58] Field of Search ..................... 424/322; 260/553 A

[56] References Cited

U.S. PATENT DOCUMENTS

| | | | |
|---|---|---|---|
| 4,080,193 | 3/1978 | Rohe et al. | 260/553 A |
| 4,127,673 | 11/1978 | Yamada et al. | 260/553 A |
| 4,129,436 | 12/1978 | Takemoto et al. | 71/120 |

*Primary Examiner*—Allen J. Robinson
*Attorney, Agent, or Firm*—Harry H. Kline

[57] ABSTRACT

A method is provided for the control of fungi attacking agronomic crops, either by contacting said fungi with a fungicidally effective amount of an alkoxyalkylurea compound, or by applying said urea to the foliage of a plant susceptible to attack by said fungi.

11 Claims, No Drawings

METHOD FOR THE CONTROL OF PHYTOPATHOGENIC FUNGI USING P-(ALKOXYALKYL)UREA COMPOUNDS

SUMMARY OF THE INVENTION

The present invention relates to a method for the control of phytopathogenic fungi with a fungicidally effective amount of a compound of formula (I):

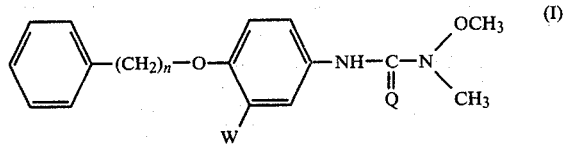

wherein W is hydrogen or Cl; Q is O or S; n is an integer of 2 to 3.

The most preferred compounds of formula (i) are:

3-[3-chloro-4-(3-phenylpropoxy)phenyl]-1-methoxy-1-methylurea;

3-[3-chloro-4-(phenethyloxy)phenyl]-1-methoxy-1-methylurea; and

3-[3-chloro-4-(phenethyloxy)phenyl]-1-methoxy-1-methyl-2-thiourea.

The fungicidal compounds of formula (i) may be conveniently prepared by the route shown below:

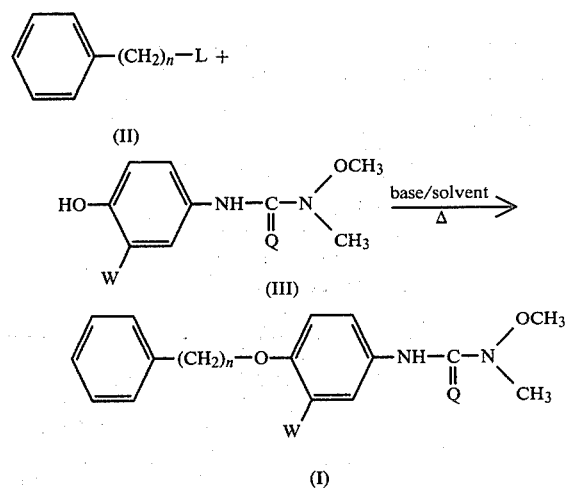

wherein W, Q and n are as hereinabove defined, and L is selected from —OSO₂CH₃ or halide. Thus, for instance, the methanesulfonate ester of the appropriate phenylalkanol, or the corresponding phenalkyl halide (L=halogen) of formula (II) is reacted with a ureidophenol of formula (III) in the presence of an organic or inorganic base, preferably potassium t-butoxide, and a solvent, such as dimethylformamide (DMF) in the temperature range of from about 20° C. to about 90° C., and preferably 60° C. to 80° C., for a period of time sufficient to essentially complete the reaction.

The methanesulfonate ester of the appropriate phenylalkanol of formula (II) and an appropriately substituted ureidophenol of formula (III) may be reacted in a two-phase system using a phase transfer catalyst, such as benzyl tributylammonium chloride, and the like, to obtain the desired fungicidal compound of formula (I), as shown below:

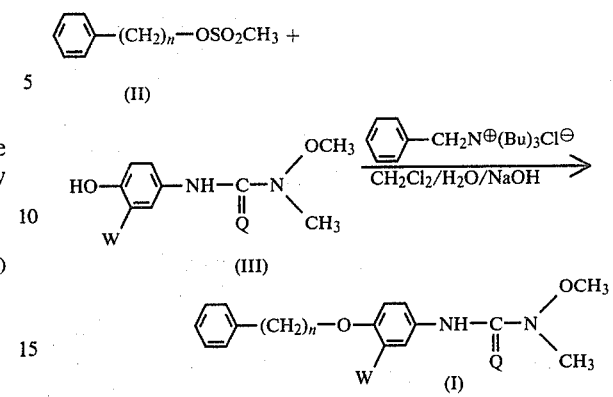

wherein W, Q and n are as hereinabove defined.

An alternate route leading to formula (I) compounds comprises, reacting an isocyanate or an isothiocyanate of formula (IV):

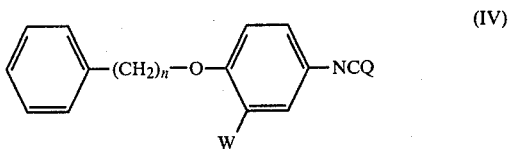

wherein Q is O or S; n is an integer of from 2 to 3; with an equimolar or excess amount of a compound of formula:

to yield the desired formula (I) compound.

The compounds of the present invention, as hereinabove defined, find utility for the control of fungi which infect living plants. They are especially useful and effective for the control of fungi, which are the causative agents for rice blast and apple scab. They are also useful for the control of powdery mildew on grains, such as wheat or barley, on vines, such as grapes, and on fruit and nut trees, such as apples, pears and pecans.

To protect plants from pathogenic fungi, the ureas of the present invention are applied to the foliage of the plant in the form of a liquid, preferably aqueous spray. Solutions or suspensions containing from about 20 ppm to about 1000 ppm, and preferably 50 ppm to 500 ppm, of formula (I) urea, are generally highly effective for this use.

The compounds of this invention can be formulated as emulsion concentrates, flowable concentrates, or wettable powders, which are diluted with water or another suitable polar solvent, generally in situ, and then applied as a dilute spray.

Usually, such sprays are applied at a rate of from about 700 l/ha to about 1900 l/ha. Obviously, smaller or larger volumes of liquid spray may be employed, depending on a plurality of factors, such as type of crop, the plant spacing, and the amount of foliage being treated.

Wettable powders can be prepared by grinding and blending together about 25% to 85% by weight of formula (I) urea, and about 75% to 15% by weight of a solid diluent, such as bentonite, diatomaceous earth, kaolin, attapulgite, and the like. To this mixture is added about 1% to 5% by weight of a dispersing agent, such as the calcium salt of a polymerized alkyl aryl sulfonic acid, sodium lignosulfonate, or the sodium salt of condensed naphthalene sulfonic acid, and about 1% to 5% by weight of a surfactant, such as polyoxyethylated vegetable oil, alkyl phenoxy polyoxyethylene ethanol, sodium alkyl sulfonate, alkyl polyoxyethylene ethers, polyoxyethylene (20) sorbitan monolaurate and monooleate, and the like, is also blended with the formulation.

Emulsion concentrates are prepared by dissolving 15% to 70% by weight of the compound in 85% to 30% by weight of a solvent, such as benzene, toluene, xylene, kerosene, 2-methoxy ethanol, propylene glycol, diethylene glycol, diethylene glycol monomethyl ether, formamide, methylformamide, and the like, and mixtures thereof. Advantageously, surfactants, such as polyoxyethylated vegetable oil, or an alkyl phenoxy polyoxyethylene ethanol, are also incorporated in amounts of 1% to 5% by weight of said concentrate.

Application of the material is made by adding a predetermined quantity of formulated product, such as described above, to the desired volume of water or other suitable solvent, alone or in combination with other agronomic chemicals for simultaneous use.

In addition of being valuable fungicides, the compounds of the present invention represented and described by formula (I), wherein W is chlorine, are valuable herbicides.

This invention is further illustrated by the examples set forth below, which are provided by way of illustration and not by way of limitation.

EXAMPLE 1

Evaluation of the Fungicidal Activity of Compounds of the Invention

To determine the effectiveness of the phenylalkoxyphenylurea compounds as fungicidal agents, a variety of pathogenic fungi, host plants and urea compounds are used in the following tests. Pathogen, host plants, the method of testing, and the rating system used are reported below, along with the data obtained.

Pathogens

RB = Rice Blast (*Piricularia oryzae*, Carv.)
AS = Apple Scab [*Venturia inaequalis* (Cke.) Wint.]

Host Plants

Rice (*Oryza sativa*)
Apple (*Malus sylvestris*)

Plants are individually grown in 5 cm peat squares and assembled in fiber flats prior to spraying. Several plants/peat square of rice and a single seedling of apple are used. Spray solutions are prepared in the final concentrations in the appropriate volume of 50% aqueous acetone. Spray to runoff is provided by two Spray System Company nozzles mounted to deliver vertical and horizontal solid cone patterns. Test plants are returned to the greenhouse immediately after application of test solutions are allowed to dry.

Plants are inoculated with aqueous spore suspensions of the respective pathogens using a DeVilbiss Atomizer and transferred to a controlled temperature/humidity cabinet (21° C.; RH 95%) for 3 days. Plants are then removed from the cabinet and transferred to the greenhouse to await disease development. Ratings are taken for disease severity on a scale of 1–7, as described below.

| Disease Rating | Disease Percentage Range | Midpoint |
|---|---|---|
| 1 | 0 | 0 |
| 2 | –8.4 | 4.2 |
| 3 | 8.5–21.4 | 14.9 |
| 4 | 21.5–78.6 | 50.0 |
| 5 | 78.7–91.6 | 85.1 |
| 6 | 91.7–99.9 | 95.8 |
| 7 | 100 | 100 |

Disease severity scores are converted to estimated percentages adjusted to the 1-7 scale from tables based on those published by Elanco for the 12-point Barrett-Horsefall rating scale. Disease percentages are then converted to percent disease control, according to the following formula:

$$\frac{\text{Disease Incidence Control (\%)} - \text{Disease Incidence Treatment (\%)}}{\text{Disease Incidence Control (\%)}} \times 100 = \text{Percent Disease Control}$$

Phytotoxicity (if present) of the compounds of the invention is indicated by the use of the following symbols:

sl = slight injury
mod = moderate injury
sv = severe injury

The word "phytotoxic" is used to indicate that all plants or treated leaves in all replicates are killed by the compound and no rating could be taken.

Data obtained are reported in Table I below.

TABLE I

Evaluation of Phenylalkoxyphenylurea Compounds for the Control of Plant Pathogenic Fungi

| Compound | Rate ppm | Percent Control of RB | AS |
|---|---|---|---|
| 3-[3-Chloro-4-(3-phenylpropoxy)-phenyl]-1-methoxy-1-methylurea | 500 | 95 | phytotoxic |
|  | 100 | 100 | 100 sv |
|  | 50 | 94 | 100 sv |
| 1-Methoxy-1-methyl-3-[4-(3-phenylpropoxy)phenyl]urea | 500 | 73 |  |
| 3-[3-Chloro-4-(phenethyloxy)phenyl]-1-methoxy-1-methylurea | 500 | 95 | phytotoxic |
|  | 100 | 97 | 100 sv |
|  | 50 | 91 | 100 sv |
| 3-[3-Chloro-4-(phenethyloxy)phenyl]-1-methoxy-1-methyl-2-thiourea | 500 | 96 |  |
|  | 100 | 94 |  |
|  | 50 | 71 |  |

EXAMPLE 2

General Procedure for the Preparation of Esters of Methanesulfonic Acid

A solution of the appropriate alcohol (0.1 mol) and triethylamine (0.15 mol) in methylene chloride (150 ml) is rapidly stirred, chilled to −15° C., and methanesulfonyl chloride (0.11 mol) added at a rate to maintain the reaction temperature below −10° C. After the addition is completed, the solution is stirred for 30 minutes in the cold, and then at room temperature for 2 hours. Next, the methylene chloride solution is separated, washed with ice-cold water, ice-cold 10% hydrochloric acid, saturated sodium bicarbonate solution, saturated brine, and then dried over magnesium sulfate. Finally, the product is isolated by evaporating the methylene chloride solution under vacuum.

Esters prepared by the above procedure are listed in Table II below.

TABLE II

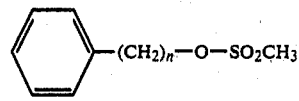

| n | Melting Point °C. | Analysis Calculated | Found | Remarks |
|---|---|---|---|---|
| 2 | amber oil | | | J.O.C. 38 1518 (1973) |
| 3 | amber oil | C, 56.04 H, 6.71 S, 14.96 | C, 55.98 H, 6.71 S, 14.94 | |

EXAMPLE 3

Preparation of 3-[(3-Chloro-4-(phenethyloxy)phenyl)-1-methoxy-1-methylurea

A mixture of 3-(3-chloro-4-hydroxyphenyl)-1-methoxy-1-methylurea (4.61 g; 0.02 mol), potassium t-butoxide (2.25 g; 0.02 mol) and DMF (200 ml) is stirred at room temperature for one hour. Mathanesulfonic acid phenethyl ester (4.0 g; 0.02 mol) is added to the above under a nitrogen atmosphere, and the mixture heated at 50° C. for 4.75 hours. The reaction mixture is then drowned in water, the aqueous mixture made slightly alkaline with 1 N sodium hydroxide solution, and extracted with methylene chloride. The organic layer is separated, washed with water, and then filtered through a layer of neutral alumina. The alumina is washed with acetonitrile, filtrate and washings are combined and evaporated under vacuum. There is obtained 6.22 g residue, a brown oil. This oil is eluted on a wet column silica gel with methylene chloride to which methanol is added slowly until the eluent is composed of 2% methanol and 98% methylene chloride. The solvent mixture is evaporated to afford 4.35 g of an off-white solid, melting point 50°–55° C. The solid is recrystallized from a heptane/toluene mixture, and the crystals dried under vacuum to afford 2.79 g of silver-white needles, melting point 60.5°–62° C.

Analysis calculated for $C_{17}H_{19}ClN_2O_3$: C, 61.00; H, 5.72; N, 8.37; Cl, 10.59. Found: C, 60,90; H, 5.82; N, 8.25; Cl, 10.49.

By substituting 3-(4-hydroxyphenyl)-1-methoxy-1-methylurea in the above reaction for 3-(3-chloro-4-hydroxyphenyl)-1-methoxy-1-methylurea, the corresponding 1-methoxy-1-methyl-3-[4-(phenethyloxy)-phenyl]urea can be obtained.

EXAMPLE 4

Preparation of 3-[3-Chloro-4-(3-phenylpropoxy)phenyl]-1-methoxy-1-methylurea

A mixture of 3-(3-chloro-4-hydroxyphenyl)-1-methoxy-1-methylurea (4.61 g; 0.02 mol), potassium t-butoxide (2.25 g; 0.02 mol) and DMF (200 ml) is stirred at room temperature for ½ hour. Methanesulfonic acid 3-phenylpropyl ester (4.29 g; 0.02 mol) is added to the above, and the mixture heated at 80° C. for 4.25 hours. The reaction mixture is cooled down, and most of the DMF removed under vacuum. Next, water, methylene chloride and a few ml of 1 N sodium hydroxide is added to the residue, and the mixture is shaken. The organic layer is then separated, washed with water, and filtered through a layer of neutral alumina. The alumina is washed with acetonitrile, filtrate and washings are combined, and evaporated under vacuum. There is obtained 6.0 g of residue, a brown oil which slowly solidifies, melting point 45°–60° C. This material is eluted on a wet column silica gel with methylene chloride to which methanol is added slowly until the eluent is composed of 2% methanol and 98% methylene chloride. The solvent mixture is evaporated under vacuum to afford 4.71 g of an off-white gum. The gum is triturated with hexane until it solidifies. The solid is collected, washed with hexane, and dried to yield 3.90 g off-white product, melting point 56°–60° C. The product is recrystallized from a mixture of hexane and heptane (ca. 375 ml) to yield 2.52 g of white crystals, melting point 58°–59° C.

Analysis calculated for $C_{18}H_{21}ClN_2O_3$: C, 61.97; H, 6.07; N, 7.91; Cl, 10.17. Found: C, 61.98; H, 6.24; N, 7.91; Cl, 10.06.

By substituting 3-(4-hydroxyphenyl)-1-methoxy-1-methylurea in the above reaction for 3-(3-chloro-4-hydroxy-phenyl)-1-methoxy-1-methylurea, the corresponding 1-methoxy-1-methyl-3-[4-(3-phenylpropoxy)-phenyl]urea can be obtained.

EXAMPLE 5

Preparation of 3-[3-chloro-4-(phenethyloxy)phenyl]-1-methoxy-1-methyl-2-thiourea.

Methoxymethylamine hydrochloride (17.53 g; 0.180 mol) is dissolved in water (100 ml), the solution made basic with sodium carbonate, and extracted with methylene chloride (300 ml). The organic layer is separated and dried over sodium sulfate. Next, a solution of 3-chloro-4-phenethoxyphenylisothiocyanate (2.79 g; 0.00963 mol) in methylene chloride (50 ml) is added, and the mixture stirred at room temperature overnight. The solvent is then removed under vacuum to yield a residual oil. This oil is then eluted on a silica gel column with hexane-ethyl acetate (1:1). The solution is then concentrated under vacuum to yield a residual oil which is recrystallized from hexane-ethyl acetate to afford 2.30 g of a white, fibrous solid, melting point 115.5°–117° C.

Analysis calculated for $C_{17}H_{19}N_2O_2SCl$: C, 58.19; H, 5.47; N, 7.98; S, 9.14; Cl, 10.11. Found: C, 57.98; H, 5.55; N, 7.92; S, 8.99; Cl, 10.00.

I claim:

1. A method for the control of plant pathogenic fungi causing apple scab, rice blast and powdery mildew comprising contacting said fungi with a fungicidally effective amount of a compound of formula:

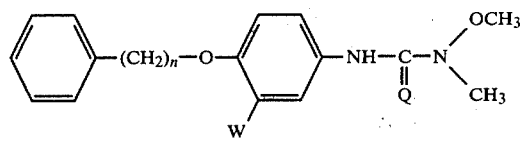

wherein W is hydrogen or Cl; Q is O or S; n is an integer of from 2 to 3.

2. A method according to claim 1, wherein Q is S.

3. A method according to claim 1, wherein said compound is 3-[3-chloro-4-(3-phenylpropoxy)phenyl]-1-methoxy-1-methylurea.

4. A method according to claim 1, wherein said compound is 3-[3-chloro-4-(phenethyloxy)phenyl]-1-methoxy-1-methylurea.

5. A method according to claim 1, wherein said compound is 3-[3-chloro-4-(phenethyloxy)phenyl]-1-methoxy-1-methyl-2-thiourea.

6. A method to protect agronomic crops from attack by plant pathogenic fungi causing apple scab, rice blast and powdery mildew comprising applying to said plants a fungicidally effective amount of a compound of formula:

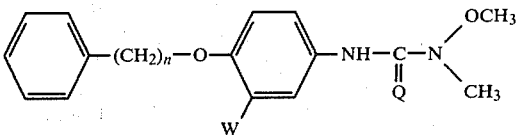

wherein W is hydrogen or Cl; Q is O or S; n is an integer of from 2 to 3.

7. A method according to claim 6, wherein Q is S.

8. A method according to claim 6, wherein said compound is 3-[3-chloro-4-(3-phenylpropoxy)phenyl]-1-methoxy-1-methylurea.

9. A method according to claim 6, wherein said compound is 3-[3-chloro-4-(phenethyloxy)phenyl]-1-methoxy-1-methylurea.

10. A method according to claim 6, wherein said compound is 3-[3-chloro-4-(phenethyloxy)phenyl]-1-methoxy-1-methyl-2-thiourea.

11. A method according to claim 6, wherein said compound is applied to said plants as a dilute spray at a concentration of from about 50 ppm to 500 ppm of said spray.

* * * * *